United States Patent [19]
Tu et al.

[11] Patent Number: 6,129,725
[45] Date of Patent: Oct. 10, 2000

[54] METHODS FOR REDUCTION OF RESTENOSIS

[76] Inventors: Lily Chen Tu; Hosheng Tu, both of 2151 Palermo, Tustin, Calif. 92782

[21] Appl. No.: 09/206,181

[22] Filed: Dec. 4, 1998

[51] Int. Cl.[7] .................................................. A61B 18/14
[52] U.S. Cl. ................................ 606/41; 606/49; 607/99; 607/113
[58] Field of Search .......................... 606/41, 49; 607/99, 607/113

[56] References Cited

U.S. PATENT DOCUMENTS

| | | | |
|---|---|---|---|
| 5,078,736 | 1/1992 | Behl | 623/1 |
| 5,178,618 | 1/1993 | Kandarpa | 606/41 |
| 5,749,914 | 5/1998 | Janssen | 607/116 |
| 5,928,217 | 7/1999 | Mikus et al. | 604/530 |
| 5,941,869 | 8/1999 | Patterson et al. | 604/508 |

*Primary Examiner*—Lee Cohen

[57] ABSTRACT

An ablation apparatus for treating tissues, tubular organs, or atherosclerosis of a blood vessel of a patient having an implanted medical stent, the ablation apparatus comprising a catheter shaft having a retracable preshaped electrode means at the distal end of the catheter shaft, the electrode means having a plurality of expandable/collapsible wire members adapted for contacting the wire members to the stent and applying RF current to treat the tissues underlying the stent for therapeutic purposes.

4 Claims, 6 Drawing Sheets

METHODS FOR REDUCTION OF RESTENOSIS

CROSS-REFERENCE TO RELATED APPLICATIONS

This application is a co-pending application of U.S. application Ser. No. 09/143,890, entitled "Ablation Apparatus and Methods for Treating Atherosclerosis" filed Aug. 31, 1998, now U.S. Pat. No. 5,980,563, Ser. No. 09/150,182, entitled "Rapid Exchange Stented Balloon Catheter Having Ablation Capabilities" filed Sep. 10, 1998, now U.S. Pat. No. 6,053,913, Ser. No. 09/157,360, entitled "Ablation Catheter and Methods for Treating Tissues" filed Sep. 19, 1998, Ser. No. 09/159,697, entitled "Ablation Device for Treating Atherosclerotic Tissues" filed Sep. 24, 1998, now U.S. Pat. No. 6,036,689, and Ser. No. 09/175,714 entitled "Dilatation Catheter Having a Bifurcated Balloon" filed Oct. 20, 1998, now U.S. Pat. No. 6,017,324, and are incorporated herein by reference.

TECHNICAL FIELD OF THE INVENTION

The present invention generally relates to improved medical apparatus and methods for treating vascular tissues, and more particularly, to such an ablation apparatus and methods for treating atherosclerosis or tissues in a patient by delivering therapeutic RF energy through a metal stenting element to the specific lesion sites for reduction of restenosis.

BACKGROUND OF THE INVENTION

An artery is one of the tube-shaped blood vessels that carry blood away from the heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or cells to the blood stream.

There are limitations, however, to this technique's application, depending on the extent of the disease, the blood flow through the artery, and the part of the anatomy and the particular vessels involved. Plaque build-up and/or severe re-stenosis recurs within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still sub-optimal. The underlying fresh tissue or cells still pose as a precursor for vessel reclosures or angio-spasm.

When a clogged artery is widened, the plaque is broken up and the underlying collagen or damaged endothelium is exposed to the blood flow. Collagen has a pro-thrombotic property that is part of body's healing processes. Unless the collagen or the damaged endothelium is passivated or modulated, the chance for blood vessel clotting as well as restenosis exist. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessels walls after the walls are treated with angioplasty and/or stenting procedures.

One method of reducing the size of cellular tissues in situ has been used in the treatment of many diseases, or as an adjunct to surgical removal procedures. This method applies appropriate heat to the tissues, and causes them to shrink and tighten. U.S. Pat. No. 5,775,338 to Hastings discloses a heated perfusion balloon for reduction of restenosis. It can be performed on a minimal invasive fashion, which is often less traumatic than surgical procedures and may be the only alternative method, wherein other procedures are unsafe or ineffective. However, the heat supplied by a heated perfusion balloon cannot exceed a blood cells' destructive temperature around 42 to 45° C.; the thermal effectiveness of this low temperature range is inadequate to treat the fresh collagen or denuded endothelium after blood vessel enlargement procedures. An alternate ablative treatment apparatus using a RF technique shall have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissues contact site to obtain the desired temperature for treating a tissue.

A stent deployed within a vessel, such as a coronary stent, has excellent metal-to-tissue contact surface. It becomes an ideal medium for applying thermal energy to the tissue needed for treatment or modulation. In the case of angioplasty alone, the enlarged blood vessel still needs certain metallic contact surface for delivering the RF thermal energy to the denuded collagen or damaged endothelium. A temporary metallic stenting element is useful in this case to shrink and tighten the target tissue. Several patents disclose a basket-type electrode catheter or a loop-type electrode catheter. Examples are U.S. PAT. No. 5,100,423 to Fearnot; U.S. Pat. No. 5,255,679 to Imran; U.S. Pat. No. 5,263,493 to Avitall; U.S. Pat. No. 5,345,936 to Pomeranz et al.; U.S. Pat.

No. 5,411,025 to Webster, Jr.; U.S. Pat. No. 5,465,717 to Imran et al.; U.S. Pat. No. 5,555,883 to Avitall; U.S. Pat. No. 5,569,244 to Hahnen; U.S. Pat. No. 5,628,313 to Webster, Jr.; U.S. Pat. No. 5,730,704 to Avitall; U.S. Pat. No. 5,738,683 to Osypka; U.S. Pat. No. 5,772,590 to Webster, Jr.; U.S. Pat. No. 5,820,568 to Willis. However, none of the above-referred patents discloses an elevate and enlarged conductive surface which are expandable/collapsible to contact the implanted stent for effective transmission of RF current to said implanted stent.

Therefore, there is a need for an improved medical apparatus having the capability to effectively contact the inner walls of a tubular vessel using the radiofrequency energy to treat an enlarged artery or other tissues, such as esophagus, larynx, uterus, urethra and the like.

SUMMARY OF THE INVENTION

In general, it is an object of the present invention to provide a method and an improved medical ablation apparatus for generating heat, to treat the atherosclerosis, vascular vessels, other tissues or tubular organs, such as intestine, colon, urethra, uterine tube, and the like. It is another object of the present invention to provide a method and an apparatus for monitoring the temperature of the ablated tissue, and to control the temperature by utilizing a temperature control mechanism and/or algorithm. The location of the temperature sensor means is preferably at close proximity of the electrode means of the ablation apparatus. It is still another object of this invention to provide a method and an apparatus for treating atherosclerosis, viscular walls, or tubular cellular tissues in a patient by applying RF current to an implanted stent and consequently to the underlying tissues. The RF current is applied continuously or intermittently in a pulsed mode. It is an object of the present invention to provide an electrode means having a plurality of expandable and collapsible wire members that have an elevated surface or a variable surface for at least one wire member for more effective contact to an implanted stent or a temporary stent.

Briefly, heat is generated by supplying a suitable energy source to an apparatus, which is comprised of an electrode means for transmitting RF current, in contact with the body tissues through an implanted stent of a temporary stent. An "implanted stent" is defined in this invention as any electrically conductive stenting element, in a mesh form, a coil form or other appropriate form that is used or implanted in a patient to enlarge and maintain the enlarged organs, tissues, or vessels. Examples include coronary stent, peripheral stent, uterine stent and the like. A "temporary stent" is defined in this invention as a stent or a stent-like electrically conductive object that is used to contact a tissue during RF current operations and is withdrawn out of the human body after use. A suitable energy source may consist of radiofrequency energy, microwave energy, ultrasonic energy, alternating current energy, or laser energy. The energy can be applied to the stent and subsequently delivered to the atherosclerotic tissues, vascular walls, or cellular tissues through the electrode means. A DIP (dispersive indifferent pad) type pad, that contacts the patient, is connected to the Indifferent Electrode Connector on the RF generator. Therefore, the RF energy deliver becomes effective when a close circuit from a RF generator through a patient and returning to the RF generator is formed. When using an alternating current outlet, the generator should be grounded to avoid electrical interference. Heat is controlled by the power of the RF current delivered and by the delivery duration. The standard RF current Generator means and its applications through the electrode means to a patient are well known for those who are skilled in the art.

In an additional embodiment, means for generating vibration at the distal section comprises a motor mounted in the cavity of the handle of a catheter, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the apparatus vibrates.

In one embodiment, the apparatus comprises a deployable and retractable electrode means for contacting an implanted stent or a temporary stent. In a preferred embodiment, the electrode means is deployable and is also expandable and collapsible so that when it expands, the outer surface contacts an implanted stent or a temporary stent wherein the outer surface may be elevated and/or enlarged for more efficient surface contact. In a preferred embodiment, the deployable electrode means comprises a variable outer surface, having varying widths with reference to the axis of the wire members. Due to the resilience and semi-compressibility of the wire members, the radially expanded wire members are expandable to its full extent when the electrode means is deployed. The outer surface of the deployed wire members is to intimately contact a stent of either an implanted stent or a temporary stent at about the outermost region of the wires; and subsequently the stent becomes an electrode means because the stent contacts the underlined tissues and RF current is applied to said tissue for a complete RF circuit. The electrode means is connected to an external RF current generator through an electrical conductor.

The method and medical apparatus of the present invention has several significant advantages over other known systems or to techniques to treat the atherosclerotic tissues having at least one implanted stent or a temporary stent. In particular, the apparatus system comprising a plurality of expandable wire members, using RF current as a heat source in this invention results in a more efficient therapeutic effect, which is highly desirable in its intended application on the atherosclerosis or on other tissue ablation applications when there is a stent.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF THE EXEMPLARY EMBODIMENTS

Referring to FIGS. 1 to 6, what is shown is a preferred embodiment of the ablation apparatus system, comprising applying radiofrequency energy to treat the atherosclerotic tissues, vascular vessels, or other tubular cellular tissues of a patient through an electrically conductive stent of either an implanted stent or a temporary stent.

Figure 1:
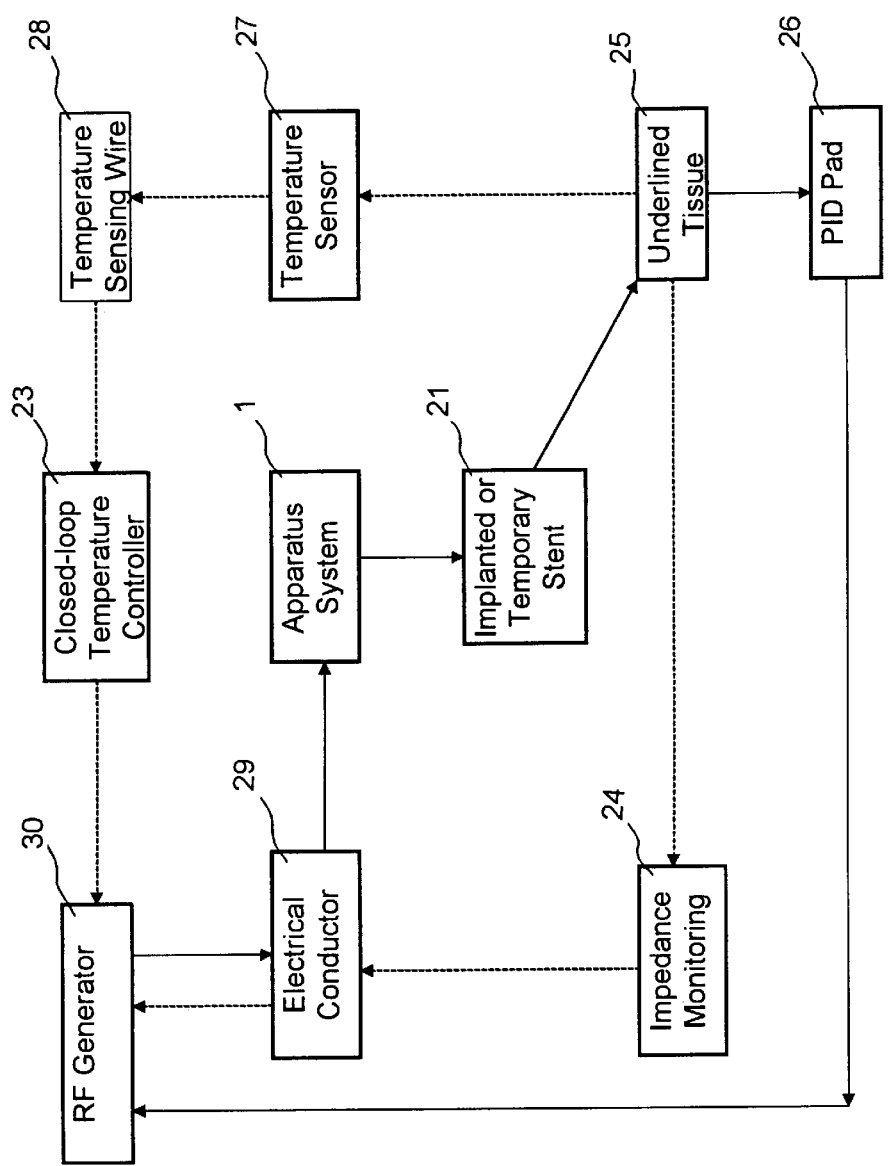
FIG. 1 is a schematic diagram of a RF treatment method in relation to the tissues or atherosclerotic tissues through an eletrically conductive stent in a patient.

FIG. 1 shows a schematic diagram of a RF treatment method in relation to the tissues or atherosclerotic tissues through an electrically conductive stent in a patient. A RF generator 30 is connected to an ablation apparatus 1 through an electrical conductor 29. An electrode means 12 of the ablation apparatus 1 is to contact a stent 21 of an implanted stent or a temporary stent when the apparatus is deployed. The stent is in close contact with the underlying tissue 25. A DIP (dispersive indifferent pad) type pad 26, that contacts the patient, is connected to the Indifferent Electrode Connector on the RF generator 30. Therefore, the RF energy delivery becomes effective when a close circuit from a RF generator through a patient and returning to the RF generator is formed. Impedance 24 measured from the tissue contact is to ensure good tissue contact for ablation, otherwise the RF current is cutoff when the impedance is unreasonably high. A temperature sensor 27 is also used to measure the tissue temperature and is relayed through a temperature sensing wire 28 and a closed-loop temperature controller 23 for controlling the ablative energy delivered. Heat is controlled by the power of the RF current delivered and by the delivery duration.

Figure 2:
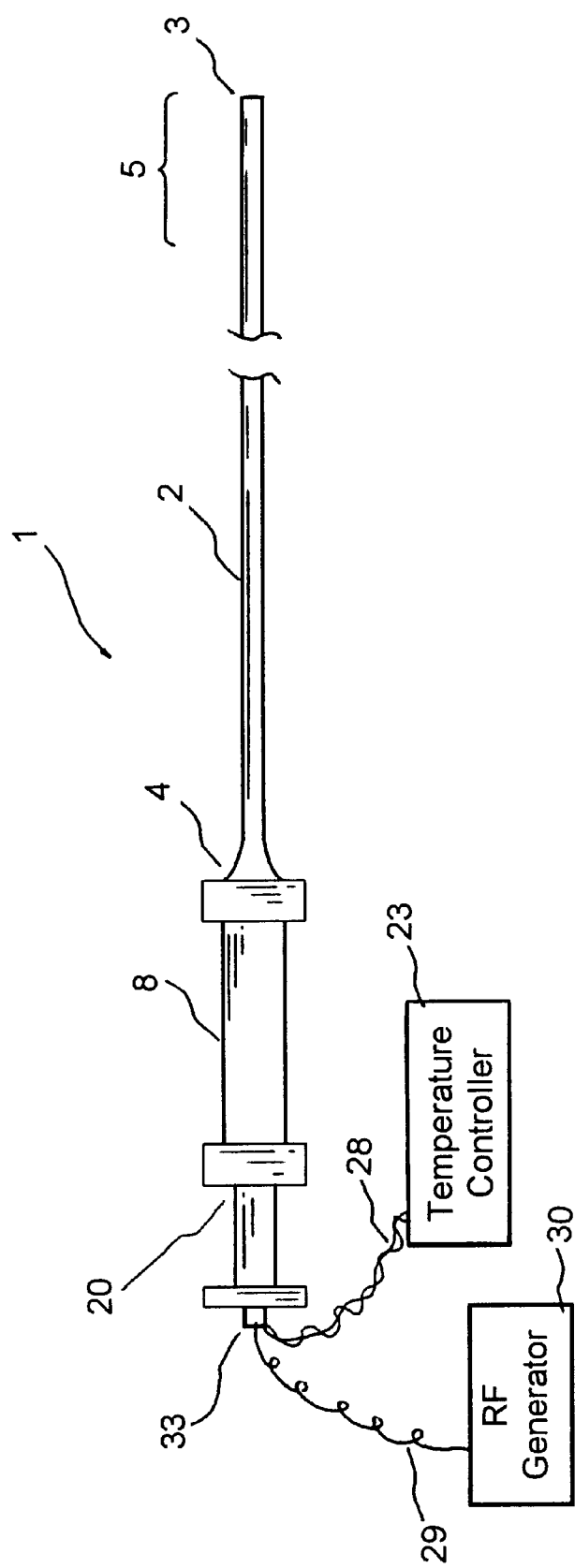
FIG. 2 is an overall view of the ablation apparatus system having a deployable electrode means and a RF generator, constructed in accordance to the principles of the present invention.

As shown in FIG. 2, an ablation apparatus system 1 comprises a catheter shaft 2 having a distal section 5, a distal end 3, proximal end 4, and at least one lumen 6 extending between the distal end 3 and the proximal end 4, wherein the at least one lumen 6 has at least one opening 7 at the distal end 3 of the catheter shaft 2. A handle 8 is attached to the proximal end 4 of the catheter shaft 2, wherein the handle 8 has a cavity. A retractable elongate element 9 is located inside the at least one lumen 6 of the catheter shaft 2. The elongate element 9 has a distal end 10 and a proximal end. A preshaped electrode means 12 for delivering a RF current is secured to the distal end 10 of the elongate element 9, wherein the electrode means 12 comprises a plurality of wire members 13, each wire member having an outer surface 14, an inner surface 15, a distal end 16 and a proximal end 17, wherein the distal ends 16 of the plurality of wire members 13 are coupled and secured to a joint 18. The plurality of wire members is expandable and collapsible radially; the outer surface 14 of each wire member has an outermost region 19 when the wire member 13 is at an expanded state. An electrode deployment mechanism 20 is mounted on the handle 8, wherein the electrode deployment mechanism is attached to the proximal end of the elongate element 9. The plurality of wire members 13 are expanded when the electrode means 12 is deployed and the plurality of wire members 13 are collapsed when the electrode means 12 is retracted. The apparatus system comprises a RF current generator 30, wherein a RF current is delivered to the electrode means 12 for therapeutic purposes.

Figure 3:
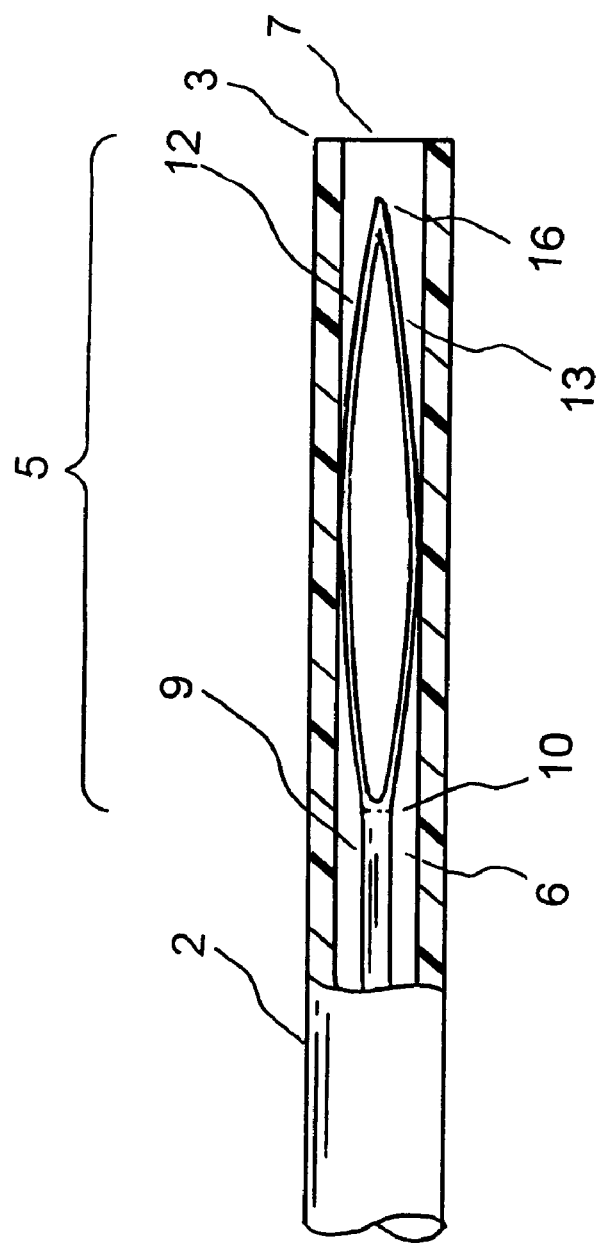
FIG. 3 is a cross-sectional view of the distal end portion of the ablation apparatus, having a deployable electrode means positioned within the lumen of the tubular shaft at a retracted, non-deployed state.

FIG. 3 shows a cross-sectional view of the distal end portion of the ablation apparatus, having a deployable electrode means positioned within the lumen of the tubular shaft at a retracted, non-deployed state. Under a non-deployed state, the deployable electrode means 12 is retracted inside the lumen 6 of the distal end portion 3 of the catheter shaft 2. The distal end 16 of the wire members 13 is located just within the distal end 3 of the tubular shaft 2. In one embodiment, the distal end 2 has two lumens. One lumen 6 is used by the deployable electrode means 12 for creating an ablation means in association with the stent 21. The other lumen having two openings at the distal tip portion 3 of the catheter shaft 2 is used to tract a previously inserted guidewire to the lesion site or stent site. The apparatus 1 of the present invention rides on an existing guidewire to the target site 35 for ablation operation.

An insulated electrical conductor 29 or the elongate element 9 itself as a conducting means for transmitting RF current passes through the lumen 6 of the shaft 2 and is connected to the electrode means 12 The other end of the electrical conductor 29 from a connector 33 on the handle 8 is connected to an external RF generator 30.

Figure 4:
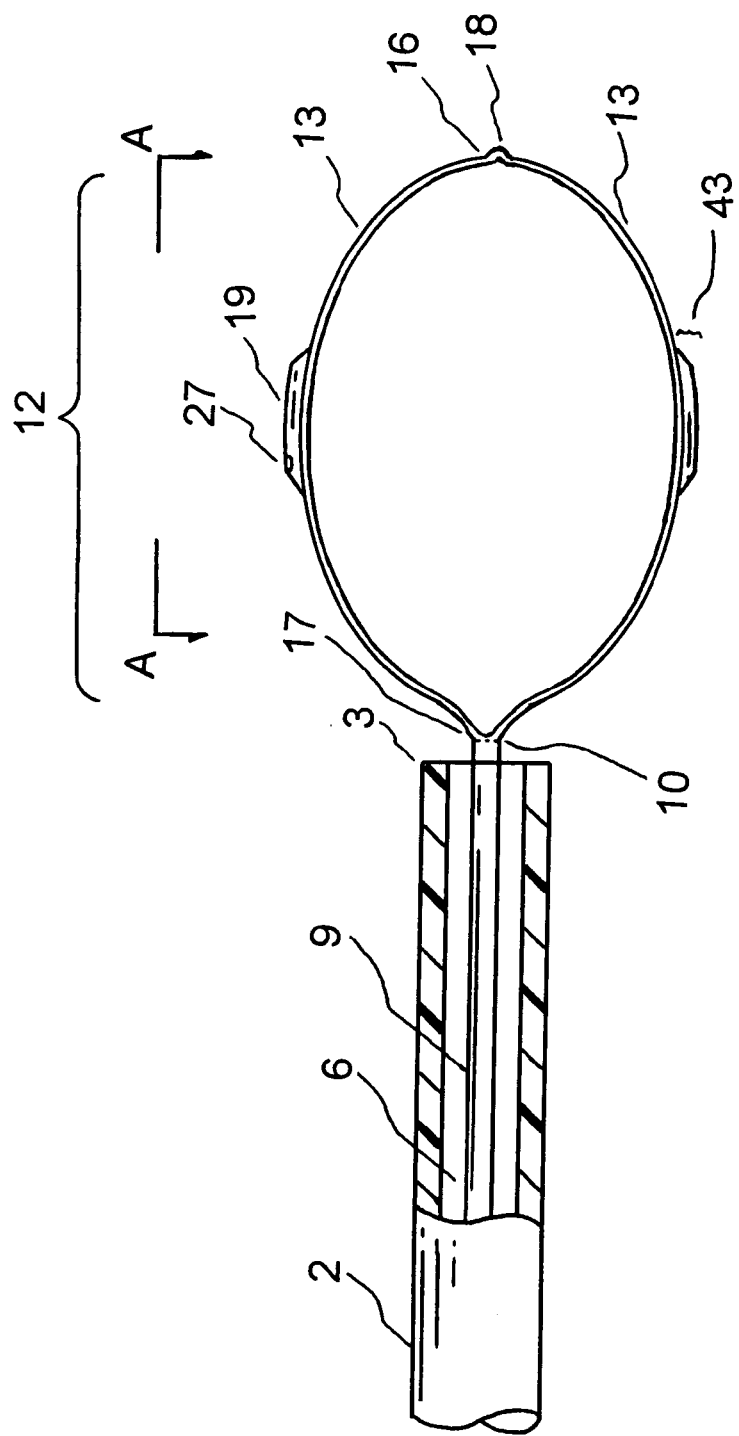
FIG. 4 is a cross-sectional view of the distal end portion of the ablation apparatus, having a deployable electrode means that is deployed to its full extent at a deployed state.

FIG. 4 shows a cross-sectional view of the distal end portion 3 of the ablation apparatus 1, having a deployable electrode means 12 that is deployed to its full extent at a deployed state. The deployment operation is initiated at the electrode deployment mechanism 20 at the handle 8. The deployed plurality of wires 13 of the electrode means 12 is fully extended radially to contact the inside surface of an electrically conductive stent 21.

In one preferred embodiment, the plurality of wire members 13 is made of a flat wire 41. In another embodiment, the plurality of wire members 13 has a variable outer surface 14 and 14A. The outer surface 14A at the outermost region 19 is more than the outer surface 14 at regions 19A, 19B close to the outermost region 19. In another preferred embodiment, the plurality of wire members 13 has an elevation 43 at the outermost region 19 of the outer surface 14A, adapted for providing an elevated outer surface for delivering RF current. The inner surface 15 of the plurality of wire members 13 may be coated with an insulating material wherein the outer surface 14 adjacent the outermost region 19 may be coated with an insulating material.

In one embodiment, at least one temperature sensor 27 is preferably disposed at close proximity of the outermost region 19 of the outer surface 14A adapted for sensing temperature signals. Insulated temperature sensing wire 28 passes from the temperature sensor 27, to an external temperature control mechanism 23 through the outlet connector 33. The RF energy delivery is controlled by using the measured temperature from the temperature sensor 27, through a closed-loop temperature control mechanism and/or algorithm. When the measured temperature rises to a preset high-limit point, the temperature control mechanism sends out a signal to cut off the RF current supply. In a similar manner, when the measured temperature drops to a preset low-limit point, the temperature control mechanism sends out a signal to activate the RF current supply.

Figure 5A:
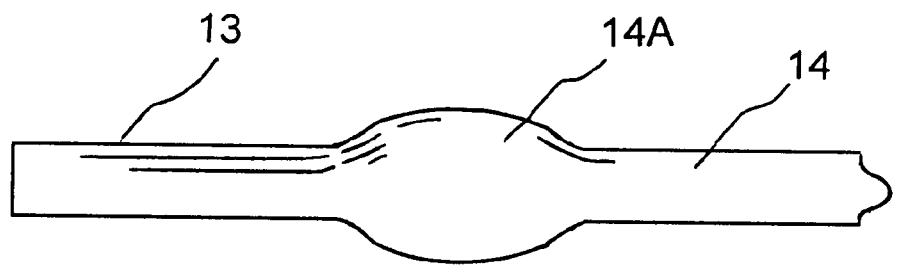
FIG. 5A is a top cross-sectional view of section A—A of FIG. 4, showing one of the wire members having an enlarged outer surface at its outermost region.
Figure 5B:
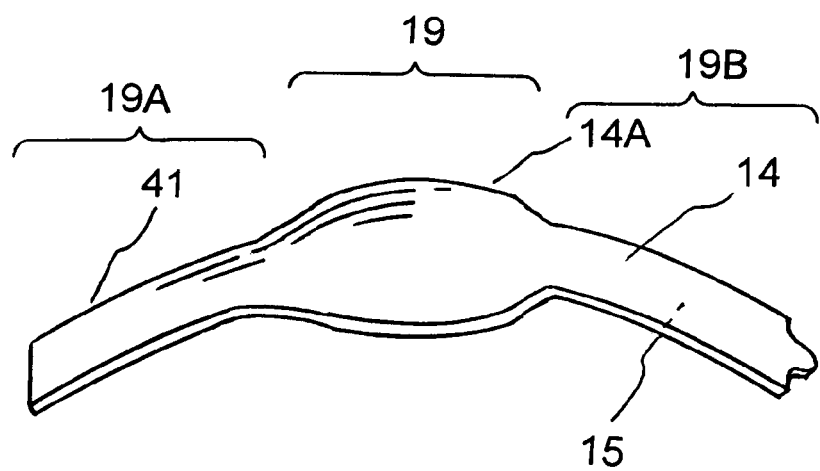
FIG. 5B is a top perspective view of section A—A of FIG. 4, showing one of the wire members having an enlarged outer surface at its outermost region.

FIG. 5A shows a top cross-sectional view of section A—A of FIG. 4, showing one of the wire members 13 having an enlarged outer surface 14A at its outermost region 19. FIG. 5B shows a top perspective view of section A—A of FIG. 4, showing one of the wire members having an enlarged outer surface at its outermost region. The enlarged outer surface 14A at the outermost region enhances RF current transmission to the stent 21 of either an implanted stent or a temporary stent.

Figure 6:
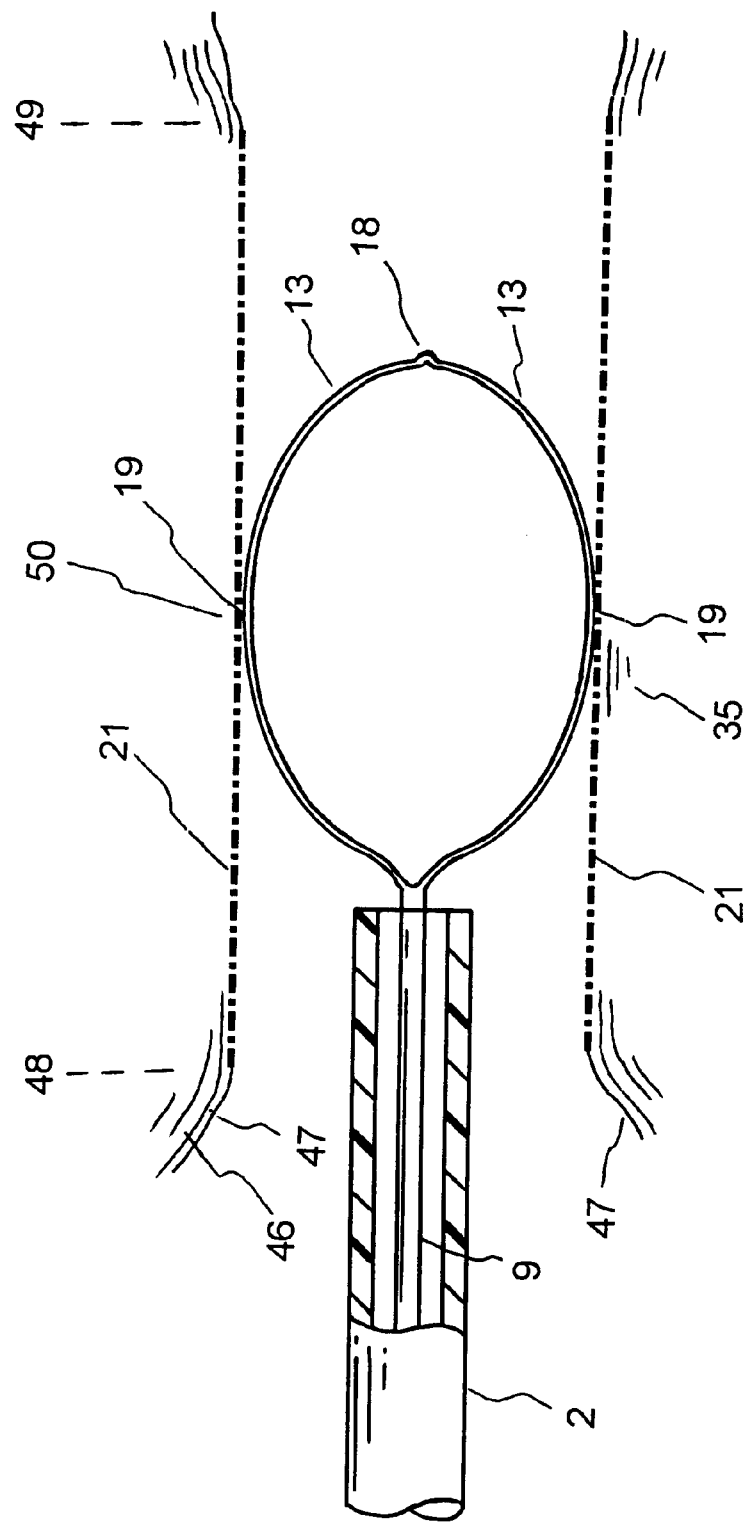
FIG. 6 is an illustrative view of the tissue underlined behind an implanted stent being treated by the ablation apparatus system of the present invention.

FIG. 6 shows an illustrative view of a tissue 25 or an atherosclerosis behind an electrically conductive stent 21 being treated by the ablation apparatus system 1 of the present invention. For illustrative purposes, the stenotic artery 46 having an arterial wall 47 is enlarged by an implanted stent 21 in a separate prior procedure. In one embodiment, the stent 21 is bordered by two imaginary lines 48 and 49. To further passivate or modulate the ruptured collagen and/or the denuded endothelium cells, RF current is delivered to the plurality wires 13 of the electrode means 12, whereby the outermost region 19 of each wire 13 contacts the sten, 21 at a contact point 50 and forms a "stent-assisted" electrode to treat the atherosclerotic tissues behind the stented region.

A method for treating a blood vessel of a patient having a stent of either an implanted stent or a temporary stent, the method comprising the steps of (a) inserting an ablation apparatus through an artery or a vein to the location of the stent, wherein the ablation apparatus comprises a catheter shaft having a distal section, a distal end, a proximal end, and at least one lumen extending between the distal end and the proximal end, wherein the at least one lumen has at least one opening at the distal end of the catheter shaft; a handle attached to the proximal end of the catheter shaft, wherein the handle has a cavity; a retractable elongate element located inside the at least one lumen of the catheter shaft, the elongate element having a distal end and a proximal end; a preshaped electrode means for delivering a RF current secured to the distal end of the elongate element, wherein the electrode means comprises a plurality of wire members, each wire member having an outer surface, an inner surface, a distal end and a proximal end, wherein the distal ends of the plurality of wire members are coupled and secured to a joint, and wherein the plurality of wire members is expandable and collapsible radially, the outer surface of each wire member has an outermost region when the wire member is at an expanded state; an electrode deployment mechanism mounted on the handle, the electrode deployment mechanism being attached to the proximal end of the elongate element, wherein the plurality of wire members are expanded when the electrode means is deployed and the plurality of wire members are collapsed when the electrode means is retracted; (b) deploying the elongate element to radially expand the plurality of wire members of the preshaped electrode means, adapted for contacting the stent; and (c) applying RF current from a RF current generator to the electrode means to effect treatment of the blood vessel.

As an alternative illustration, a method for treating a tubular organ of a patient having a stent of either an implanted stent or a temporary stent, the method comprising the steps of (a) inserting an ablation apparatus through a natural opening to the location of the stent, wherein the ablation apparatus system comprises a tubular shaft having a retractable preshaped electrode means, wherein the electrode means has an electrical conductor and a plurality of expandable wire members, adapted for the expanded wire members to contact the stent; (b) deployed the preshaped electrode means to radially expand the plurality of wire members to contact the stent; and (c) applying RF current from a RF current generator through the electrical conductor to the plurality of expanded wire members of the electrode means to effect treatment of the tubular organ of a patient.

The external RF current generator has the capability to supply RF current by controlling the time, power, and temperature through an optional separate closed-loop temperature controller. The patient is connected to the RF generator through a DIP electrode to form a closed-loop current system. Therefore, RF current is applied and delivered to the targeted atherosclerosis region, through the electrode means of this invention, the "stent-assisted" electrode means. The radiofrequency energy current in this invention is preferably within the range of 50 to 2,000 kHz. The frequency of the vibration of the medical apparatus in this invention is preferably within the range of 60 to 1000 cycles per minute. By simultaneously applying RF energy to the electrode and by applying the pressure or vibration therapy, the atherosclerotic tissues can be treated.

In a particular embodiment, the material for the electrode means of this invention consists of conductive metals such as platinum, iridium, gold, silver, stainless steel, Nitinol, or an alloy of these metals.

From the foregoing description, it should now be appreciated that an ablation apparatus system for the tubular organs, therosclerotic tissues, and the treatment of vascular tissues, comprising a suitable energy source and/or a pressure therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for treating a blood vessel of a patient having a stent of an implanted stent or a temporary stent, the method comprising the steps of:

(a) inserting an ablation apparatus through an artery or a vein to the location of the stent, wherein the ablation apparatus comprises a catheter shaft having a distal section, a distal end, a proximal end, and at least one lumen extending between the distal end and the proximal end, wherein the at least one lumen has at least one opening at the distal end of the catheter shaft; a handle attached to the proximal end of the catheter shaft, wherein the handle has a cavity; a retractable elongate element located inside the at least one lumen of the catheter shaft, the elongate element having a distal end and a proximal end; a preshaped electrode means for delivering RF current secured to the distal end of the elongate element, wherein the electrode means comprises a plurality of wire members, each wire member having an outer surface, an inner surface coated with an insulating material, a distal end and a proximal end, wherein the distal ends of the plurality of wire members are coupled and secured to a joint, and wherein the plurality of wire members is expandable and collapsible radially, the outer surface of each wire member has an outermost region and said outer surface adjacent said outermost region is coated with an insulating material when the wire member is at an expanded state; an electrode deployment mechanism mounted on the handle, the electrode deployment mechanism being attached to the proximal end of the elongate element, wherein the plurality of wire members are expanded when the electrode means is deployed and the plurality of wire members are collapsed when the electrode means is retracted;

(b) deploying the elongate element to radially expand the plurality of wire members of the preshaped electrode means, wherein said outermost regions contract the stent; and (c) applying RF current from a RF current generator to the electrode means to effect treatment of the blood vessel.

2. The method for treating a blood vessel of a patient having a stent of an implanted stent or a temporary stent as in claim 1, wherein the RF current is within the range of 50 to 2,000 kHz.

3. A method for treating a tubular organ of a patient having a stent, the method comprising the steps of:

(a) inserting an ablation apparatus through a natural opening to the location of the stent, wherein the ablation apparatus comprises a tubular shaft having a retractable preshaped electrode means for delivering RF current, wherein the electrode means has an electrical conductor and a plurality of expandable wire members, wherein said expandable wire members are coated with in insulating material except for a region of said expanded wire members to contact the stent;

(b) deploying the preshaped electrode means to radially expand the plurality of wire members, wherein the uninsulated regions contact the stent; and (c) applying RF current from a RF current generator through the electrical conductor to the plurality of expanded wire members of the electrode means to effect treatment of the tubular organ of a patient.

4. The method for treating a tubular organ of a patient having a stent as in claim 3, wherein the RF current is within the range of 50 to 2,000 kHz.

* * * * *